US007230122B2

United States Patent
Liu et al.

(10) Patent No.: US 7,230,122 B2
(45) Date of Patent: Jun. 12, 2007

(54) SULFONIUM SALT PHOTINITIATORS AND USE THEREOF

(75) Inventors: Yuxia Liu, Dayton, NJ (US); Donald E. Herr, Doylestown, PA (US)

(73) Assignee: National Starch and Chemical Investment Holding Corporation, New Castle, DE (US)

(*) Notice: Subject to any disclaimer, the term of this patent is extended or adjusted under 35 U.S.C. 154(b) by 108 days.

(21) Appl. No.: 10/700,754

(22) Filed: Nov. 4, 2003

(65) Prior Publication Data

US 2005/0095528 A1    May 5, 2005

(51) Int. Cl.
*G03F 7/004* (2006.01)

(52) U.S. Cl. .............................. 549/27; 556/80; 522/31; 430/270.1

(58) Field of Classification Search ...................... None
See application file for complete search history.

(56) References Cited

U.S. PATENT DOCUMENTS

| | | | |
|---|---|---|---|
| 4,231,951 A | 11/1980 | Smith et al. ................... | 556/80 |
| 4,694,029 A | 9/1987 | Land et al. ..................... | 522/8 |
| 5,010,118 A | 4/1991 | Desorcie et al. ............... | 522/31 |
| 5,082,686 A | 1/1992 | Desorcie et al. ............ | 427/515 |
| 5,414,092 A | 5/1995 | Green et al. ................... | 549/27 |
| 2004/0242901 A1 | 12/2004 | Norcini | |

FOREIGN PATENT DOCUMENTS

| | | |
|---|---|---|
| EP | 1481973 | 12/2004 |
| JP | 10007649 | 4/1998 |
| JP | 10-212286 | 8/1998 |
| JP | 11-269169 | 10/1999 |
| WO | WO 03/002557 | 1/2003 |
| WO | WO 03/008404 | 1/2003 |
| WO | WO 03/072567 | 9/2003 |

OTHER PUBLICATIONS

Dektar et, al."Photochemistry of Triarylsulfonium Salts" J. Am. Chem. Soc., vol. 112, 1990, pp. 6004-6015, XP002326263.
Pisula et al. "Exceptionally long-Range Self-Assembly of Hexa-peri-hexabenzocoronene with Dove-Tailed Alkyl Substituents" J. Am. Chem. Soc., vol. 126, Apr. 6, 2004, pp. 8074-8075.

*Primary Examiner*—Barbara L. Gilliam
(74) *Attorney, Agent, or Firm*—Cynthia L. Foulke; Sun Hee Lehmann

(57) ABSTRACT

Sulfonium salt photoinitiator compositions, precursors useful in the preparation of such photoinitiators and the use of these photoinitiators in, e.g., UV curable adhesives, UV curable sealants, UV curable coating compositions, such as printing inks and varnishes, and UV curable encapsulants.

11 Claims, 1 Drawing Sheet

SULFONIUM SALT PHOTINITIATORS AND USE THEREOF

FIELD OF THE INVENTION

Figure 1:
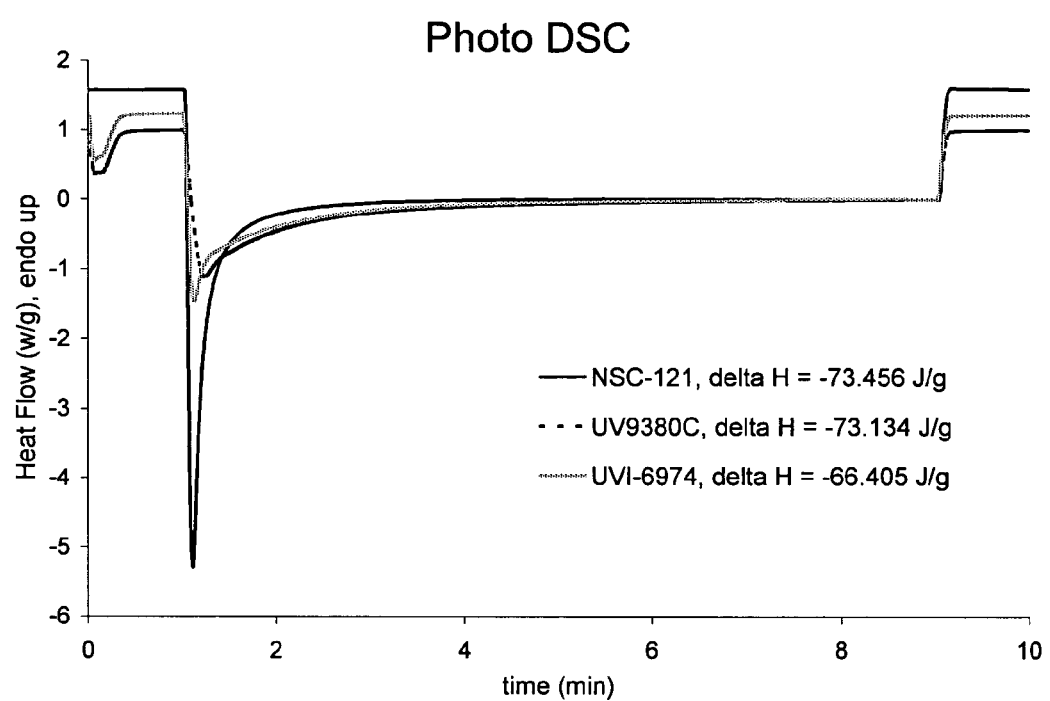

The present invention relates to sulfonium salt photoinitiators, their synthesis and to their use in UV curable compositions.

BACKGROUND OF THE INVENTION

The primary function of a photoinitiator is to initiate polymerization when the photoinitiator is irradiated with e.g., ultraviolet (UV) radiation. There are two main types of photoinitiators that can be used to initiate polymerization in the monomer or prepolymer upon irradiation—radical photoinitiators and cationic photoinitiators.

The most frequently used cationic photoinitiators are either organic iodonium or sulfonium salts. The mechanism by which a cationic photoinitiator acts, when irradiated, is that it forms an excited state which then breaks down to release a radical cation. This radical cation reacts with the solvent, or another hydrogen atom donor, eventually generating a protonic acid. The active species that initiates the polymerization is the protonic acid.

There continues to be a need in the art for cationic polymerization photoinitiators, including novel sulfonium salts, that can advantageously be used in UV curable compositions. The present invention addresses this need.

SUMMARY OF THE INVENTION

The invention is directed to precursor compounds useful in the preparation of sulfonium salt photoinitiators, sulfonium salt photoinitiators, and the use of the precursor compounds in the invention in the preparation of sulfonium salt photoinitiators.

One aspect of the invention is directed to precursor compounds. In one preferred embodiment, the precursor is 1-bromo-2-decyl-tetradecane. In another preferred embodiment, the precursor is a thioxanthone derivative containing linear or branched alkyl or alkoxy groups. In still another preferred embodiment the precursor is a benzophenone derivative. The thioxanthone and benzophenone derivatives may be used as photoinitiators, or may be used as precursors in the preparation of sulfonium salt photoinitiators.

Another aspect of the invention is directed to sulfonium salt photoinitiators, more specifically, organic soluble and red-shifted sulfonium salt photoinitiators containing chromophores of aromatic ketones containing linear or branched alkyl or alkoxy groups.

Still another aspect of the invention is directed to UV curable compositions comprising a soluble and red shifted sulfonium salt photoinitiator. Included are adhesives, inks and coatings. Preferred are epoxy based UV curable compositions.

In a preferred embodiment, the UV composition is an UV curable hot melt pressure sensitive or laminating adhesive. Preferred adhesives are epoxidized block copolymer-based UV curable pressure sensitive adhesives comprising a sulfonium salt photoinitiator. Particularly preferred are radiation curable adhesives comprising an epoxidized block copolymer, a saturated block copolymer and/or a rosin derived alcohol, and a sulfonium salt photoinitiator. The adhesives of the invention may optionally comprise a hydrocarbon resin, a rosin and/or rosin ester, and an oil.

Yet another aspect of the invention is directed to articles of manufacture comprising UV curable or cured adhesive and/or coating compositions.

BRIEF DESCRIPTION OF THE DRAWING FIGURES

FIG. 1 is a photo DSC analysis of photocurable compositions containing a sulfonium salt photoinitiator of the invention (Example 21), a commercially available sulfonium salt photoinitiator (UVI-974) and a commercially available iodonium salt photinitiator (UV9380C).

DETAILED DESCRIPTION OF THE INVENTION

The disclosures of all references cited herein are incorporated in their entireties by reference.

The current invention provides cationic photoinitiators, in particular, sulfonium salt photoinitiators, more particularly soluble and red-shifted sulfonium salt photoinitiators containing chromophores of aromatic ketones containing linear or branched alkyl or alkoxy groups. Also proved are precursor compounds useful in the manufacture of sulfonium salt photoinitiators, and adhesives, inks, coating compositions and the like comprising the sulfonium salt photoinitiators of the invention.

A novel class of soluble and red-shifted sulfonium salt photoinitiators have been discovered that have increased solubility in UV curable compositions, promote efficient thick film UV curing, exhibit increased thermal stability in UV curable compositions before UV cure, exhibit increased curing rates, and have a reduced dark cure time.

In one embodiment of the invention, the photoinitiators have the structural formula (I):

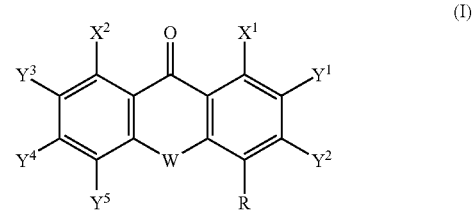

where
$X^1$ and $X^2$ are independently Cl, Br, I, F, H, alkyl or alkoxy, wherein at least one of $X^1$ or $X^2$ is not a hydrogen,
$Y^1$, $Y^2$, $Y^3$, $Y^4$ and $Y^5$ are independently Z, R, or $X^{1\ or\ 2}$, wherein at least one of $Y^1$, $Y^2$, $Y^3$, $Y^4$ or $Y^5$ is Z,
Z is $SAr_2^+ \cdot M^-$, wherein Ar is phenyl, $C_{1-24}$ alkyl phenyl, $C_{1-24}$ alkoxyphenyl, acyl, thiophenyl, phenylthiophenyl, $C_{1-24}$ alkylthiophenyl, $C_{1-24}$ dialkyl substituted phenylthiophenyl, or $C_{1-24}$ dialkoxy substituted phenylthiophenyl, and $M^-$ is $SbF_6^-$, $PF_6^-$, $AsF_6^-$, $BF_4^-$, $B(C_6F_5)_4^-$ or $Ga(C_6F_5)_4^-$,
W is O, S, NR or $CH_2$, and
R is $C_{1-24}$ alkoxy, $C_{1-24}$ alkyl, aryl, Cl, Br, I, F, or H.

A preferred photoinitiator of the structural formula I is represented by the structural formula (IA).

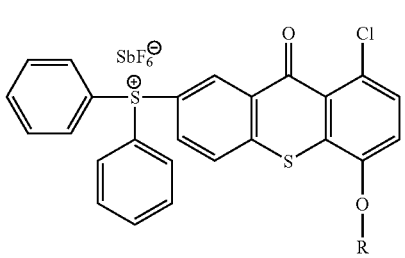

where R is $C_3H_7$, $C_{12}H_{25}$ or $C_{24}H_{49}$.

In a second embodiment of the invention, the photoinitiators have the structural formula (II):

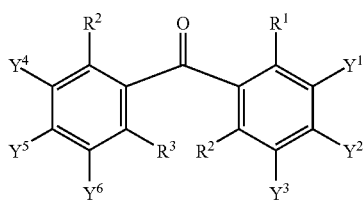

where
$R^1$, $R^2$, $R^3$ and $R^4$ are independently a $C_{1-24}$ alkoxy, a $C_{1-24}$ alkyl, an aryl, H, Cl, Br, I or F, wherein at least one of $R^1$, $R^2$, $R^3$ or $R^4$ is a halogen,
$Y^1$, $Y^2$, $Y^3$, $Y^4$, $Y^5$ and $Y^6$ are independently Z or $R^{1-4}$, wherein at least one of $Y^1$, $Y^2$, $Y^3$, $Y^4$, $Y^5$ or $Y^6$ is Z,
Z is $SAr_2^+.M^-$, wherein Ar is phenyl, $C_{1-24}$ alkyl phenyl, $C_{1-24}$ alkoxyphenyl, acyl, thiophenyl, phenylthiophenyl, $C_{1-24}$ alkylthiophenyl, $C_{1-24}$ dialkyl substituted phenylthiophenyl, or $C_{1-24}$ dialkoxy substituted phenylthiophenyl, and $M^-$ is $SbF_6^-$, $PF_6^-$, $AsF_6^-$, $BF_4^-$, $B(C_6F_5)_4^-$ or $Ga(C_6F_5)_4^-$.

A preferred photoinitiator of the structural formula II is represented by the formula (IIA):

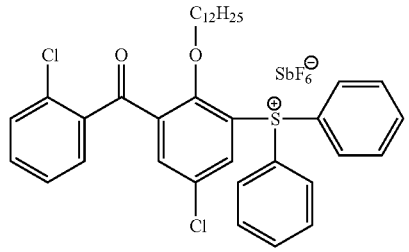

where R is $C_{12}H_{25}$ or $C_{24}H_{49}$.

In a third embodiment of the invention, the photoinitiators have the structural formula (III):

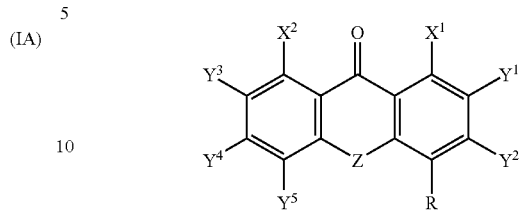

where
$X^1$ and $X^2$ are independently Cl, Br, I, F, H, alkyl or alkoxy, wherein one of $X^1$ or $X^2$ is preferred to be a halogen,
$Y^1$, $Y^2$, $Y^3$, $Y^4$ and $Y^5$ are independently R, or $X^{1\ or\ 2}$,
Z is $SAr^+.M^-$, wherein Ar is phenyl, $C_{1-24}$ alkyl phenyl, $C_{1-24}$ alkoxyphenyl, acyl, thiophenyl, phenylthiophenyl, phenylsulfoxyphenyl, phenylsulfonylphenyl, $C_{1-24}$ alkylthiophenyl, $C_{1-24}$ dialkyl substituted phenylthiophenyl, or $C_{1-24}$ dialkoxy substituted phenylthiophenyl, and $M^-$ is $SbF_6^-$, $PF_6^-$, $AsF_6^-$, $BF_4^-$, $B(C_6F_5)_4^-$ or $Ga(C_6F_5)_4^-$, and
R is $C_{1-24}$ alkoxy, $C_{1-24}$ alkyl, aryl, Cl, Br, I, F or H.

A preferred photoinitiator of the structural formula III is represented by the by the structural formula (IIIA):

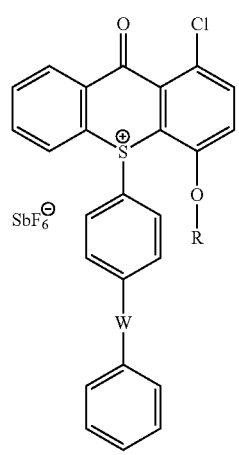

where R is $C_3H_7$, $C_{12}H_{25}$ or $C_{24}H_{49}$, W is S, SO, $SO_2$ or CO.

Another preferred photoinitiator of the structural formula III is represented by the by the structural formula (IIIB):

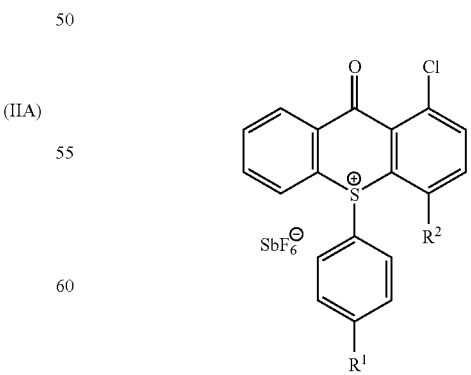

where $R^1$ and $R^2$ are independently H, $CH_3$, $C_2H_5$, $C_3H_7$, $C_{12}H_{25}$, $C_{24}H_{49}$, $OCH_3$, $OC_2H_5$, $OC_3H_7$, $OC_{12}H_{25}$ or $OC_{24}H_{49}$.

Yet another preferred photoinitiator of the structural formula III is represented by the by the structural formula (IIIC):

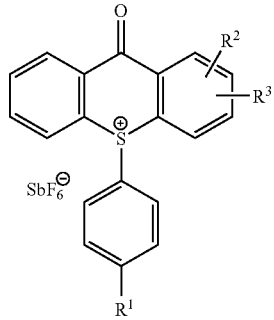

(IIIC)

where $R^1$, $R^2$ and $R^3$ are independently H, $CH_3$, $C_2H_5$, $C_3H_7$, $C_{12}H_{25}$, $C_{24}H_{49}$, $OCH_3$, $OC_2H_5$, $OC_3H_7$, $OC_{12}H_{25}$ or $OC_{24}H_{49}$.

The invention encompasses precursor compounds used to prepare the photoinitiators of the invention. One precursor of the invention used to prepare the sulfonium salt photoinitiators of the invention is 1-bromo-2-decyl-tetradecane, which has the following structural formula:

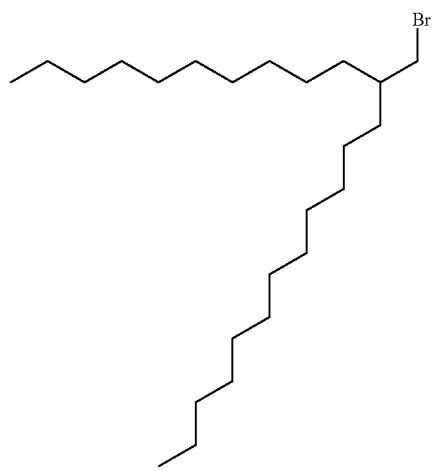

Other precursors of the invention include thioxanthone derivatives containing linear or branched alkyl or alkoxy groups. While these compounds may be used as precursors to prepare the sulfonium salt photoinitiators, they also act as photoinitiators. The use of these compounds as photoinitiators for use in photocurable adhesives, coatings, inks and the like is encompassed by the invention.

The thioxanthone derivatives of the invention include 1-chloro-4-hydroxythioxanthone, which has the following structural formula:

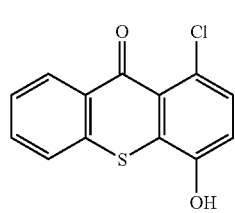

1,2-dichloro-4-hydroxythioxanthone, which has the following structural formula:

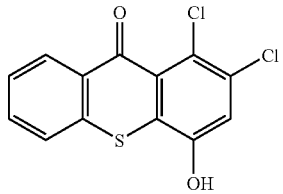

1-chloro-4-hydroxy-2-methylthioxanthone, which has the following structural formula:

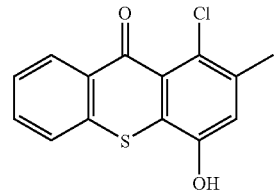

1-chloro-4-hydroxy-3-methylthioxanthone, which has the following structural formula:

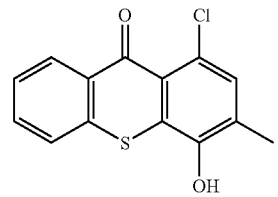

1-chloro-4-dodecyloxythioxanthone, which has the following structural formula:

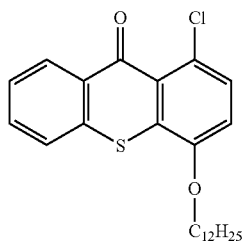

1,2-dichloro-4-dodecyloxythioxanthone, which has the following structural formula:

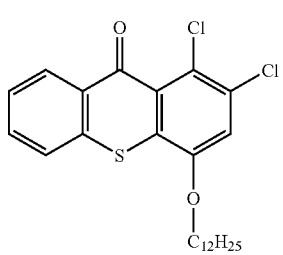

1-chloro-4-dodecyloxy-2-methylthioxanthone, which has the following structural formula:

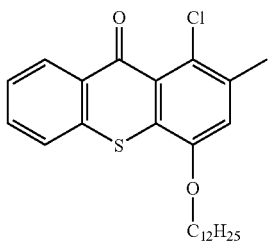

1-chloro-4-dodecyloxy-3-methylthioxanthone, which has the following structural formula:

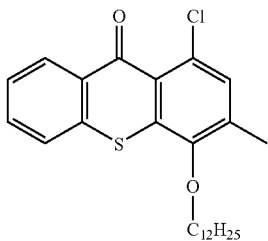

Included thioxanthone precursors of the invention encompass, for example, 1-chloro-4-(2-decyltetradecyl-1-oxy) thioxanthone, which has the following structural formula:

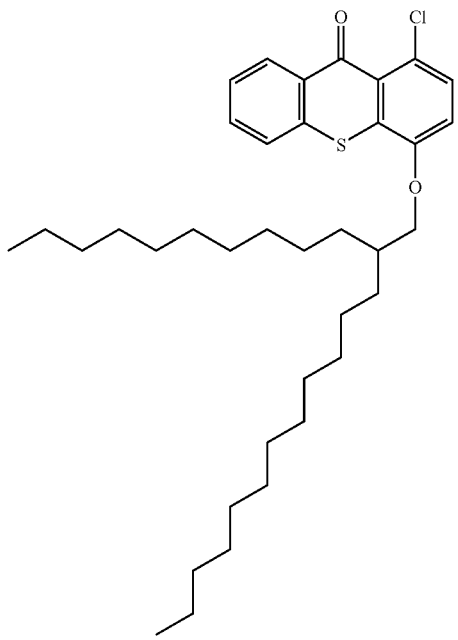

Still other precursors of the invention include benzophenone derivatives. While these compounds may be used as precursors to prepare the sulfonium salt photoinitiators, they also act as photoinitiators. The use of these compounds as photoinitiators for use in photocurable adhesives, coatings, inks and the like is encompassed by the invention.

The benzophenone derivatives of the invention include 2',5-dichloro-2-dodecyloxybenzophenone, which has the following structural formula:

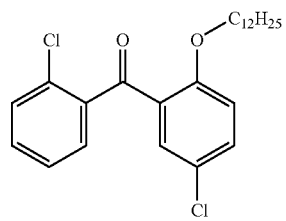

Still other precursors used to prepare the photoinitiators of the invention include 4,4'-didodecyloxyphenyl sulfide and 4,4'-didodecyloxylphenyl sulfoxide which, respectively, have the following structural formulas:

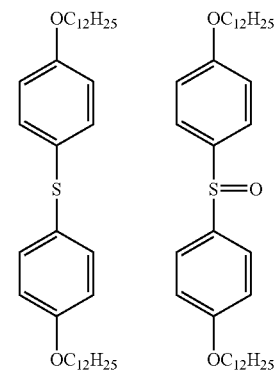

The polymeric photoinitiators of the invention may be used to prepare a wide variety of radiation curable materials including pressure sensitive hot melt adhesives, inks and coating compositions. Photocurable compositions contemplated for use include compositions comprising a photoinitiator of the formulation I, II and/or III. Particularly preferred photoinitiators are those having the structural formula IIIA, B and C. When used in the formulation of sealants or coating compositions, photoinitiators having the formula IIIA with R is $C_3H_7$ or $C_{12}H_{25}$; IIIB with $R^1$ is $C_{12}H_{25}$ and $R^2$ is $OC_3H_7$ or $OC_{12}H_{25}$ are particularly preferred. When used in the formulation of adhesive compositions, photoinitiators having the formula IIIA with R is $C_{12}H_{25}$ or $C_3H_7$ are particularly preferred.

Relative to typical commercially available photoinitiators, the photoinitiators of the invention have increased solubility in UV curable compositions (particularly in compositions that are hydrophobic), promote efficient thick film UV curing, exhibit increased thermal stability in UV curable compositions before UV cure, and have increased curing rates and reduced dark cure time.

The use of the term coating compositions is used broadly herein to mean decorative and abrasion resistant coatings, lacquers, varnishes, fiber reinforced composites, microelectronic encapsulations, fiber optic coatings, molding compounds, UV-set structural resins and the like.

The radiation curable adhesives of the invention may, desirably, be formulated as a "hot melt," a "warm melt" or a liquid adhesive, and formulated to be pressure sensitive or not. "Hot melt" adhesives are defined here as those applied at temperatures of from about 250° F. to about 400° F., whereas "warm melt" adhesives are applied at temperature above ambient but below 250° F. "Liquid" adhesive require no heat for their application; being are applied at ambient conditions.

As used herein, the term "pressure-sensitive adhesive" refers to a viscoelastic material which adheres instantaneously to most substrates with the application of slight pressure and remains permanently tacky. Pressure sensitive adhesives are bondable at ambient conditions indefinitely. Non-pressure sensitive adhesives are used to form bonds while in the molten state, i.e., they are applied hot to the substrate and bonded to the second substrate prior to setting. Once set they have little if any tack or bondability. One cannot coat these types of adhesives onto one substrate and create a bond with them to a second substrate at a later date at ambient conditions as can be done with a true pressure sensitive.

The term "curable" is used herein in its conventional sense as meaning capable of forming covalent cross-links.

The term "radiation-curable adhesive" as used herein means an adhesive composition that is curable upon exposure to actinic and/or ionizing radiation. The term "radiation" is used herein to include actinic radiation such as ultraviolet radiation and ionizing radiation created by the emission of electrons or highly accelerated nuclear particles such as neutrons, alpha-particles etc.

While the invention will hereinafter be described in terms of the use of the photoinitiators in an adhesive formulation, it is understood that the invention is not to be so limited thereto.

Preferred radiation curable adhesives comprise, as the base polymer, at least one epoxidized block copolymer capable of UV cationic curing. Epoxidized block copolymers which may be used in the practice of the invention include those described in U.S. Pat. Nos. 5,229,464, 5,491,193, 5,516,824, 5,686,535, 5,776,998, and 5,837,749, and are commercially available from Kraton Polymers. Both radial and linear epoxidized block copolymers may be used in the practice of the invention for use. A preferred epoxidized block copolymer which may be used in the practice of the invention is EKP 207 (Kraton Polymers), a diblock copolymer prepared by the sequential polymerization of isoprene and butadiene, followed by hydrogenation and epoxidation. EKP 207 contains about 11 epoxide groups per molecule.

The adhesive of the invention will typically comprise about 10% to about 60% of the epoxidized block copolymer.

Saturated block copolymers consist of materials of the structure $(A-B_n-A)$, or $(A-B)_n-X$, or $(A-B)_n$, or $(A-B)_n-X-C_m$ wherein X is a multivalent coupling agent with functionality m+n of two or more, and polymer blocks A are non-elastomeric polymer blocks and polymer blocks B are saturated elastomeric blocks, and polymer blocks C are either saturated or unsaturated, preferably unsaturated elastomeric blocks. Saturated blocks are substantially hydrogenated such that the majority of olefinic groups have been eliminated. Copolymers useful in the present invention may be linear or radial; with radial copolymers the functionality of X is three or more. Some levels of diblock copolymer, A-B, may be present by design or due to incomplete coupling of the A-B arms to X. Diblock is beneficial for increasing tack, peel and open time, but reduces cohesive strength and resistance to cold flow prior to cure.

Examples of multifunctional coupling agents, "X", include dibromoethane with functionality of 2; trisnonylphenyl phosphite and trichloromethyl silane, both with functionality of 3; and tetra chlorosilane with functionality of 4.

The non-elastomeric blocks A may comprise homopolymers or copolymers of vinyl monomers such as vinyl arenes, vinyl halides, and vinyl carboxylates, as well as acrylic monomers such as acrylonitrile, methacrylonitrile, esters of acrylic acids, etc. Monovinyl aromatic hydrocarbons include styrene, vinyl toluene, vinyl xylene, ethyl vinyl benzene as well as dicyclic monovinyl compounds such as vinyl naphthalene and the like. Other non-elastomeric polymer blocks may be derived from alpha olefins such as vinyl cyclohexane, or other rigid olefins such as norbornene, pinene, and the like. Styrene is preferred, in an amount comprising less than 45% by weight of the total copolymer composition, more preferably 15 to 25%, however it is most preferred that the least amount of styrene possible is used in order to maximize the softness and flexibility of the final cured adhesive, while still forming hard styrene domains upon cooling to produce a solid adhesive. The elastomeric blocks B and C are derived from a diene or dienes (preferably isoprene and/or butadiene). The B blocks are substantially hydrogenated (saturated) by means well known in the art. It is preferred that the C blocks, if present, are not hydrogenated, and most preferably are isoprene. Suitable saturated block copolymers include SEBS (polystyrene end blocks with a hydrogenated butadiene midblock) and SEPS (polystyrene end blocks with a hydrogenated isoprene midblock). Polymers high in diblock (SEB or SEP) are preferred. High levels are those above 10%, with levels above 25% preferred, and levels of above 40% most preferred. Block copolymer molecules with more than one hard (high Tg) A block provide the adhesive with strength and resistance to cold-flow (the resistance to slumping in the unsupported state at ambient conditions) prior to cure. Diblock copolymer molecules improve the pressure sensitivity of the final cured adhesive. Even more preferred are radial block copolymers in which both functions-strength and pressure sensitivity-are derived from one molecule. These radial materials contain hard A blocks at the ends of at least two of the arms and one or more arms consisting of C blocks. The latter arms are termed free arms or pendant arms since they are not linked into the hard domains when the adhesive cools (no A block). These pendant arms are derived form diene monomers and may be saturated (via subsequent hydrogenation) or unsaturated. Preferably these pendant arms are derived from isoprene. An example of such a material is GRP 6919, also referred to as "Tacky G", a $(SEB)_2-X-(I)_2$ radial block copolymer available from Kraton Polymers.

Adhesives of the invention will typically comprise about 3% to about 30%, more preferably from about 5% to about 15%, of the styrenic block copolymer.

Suitable rosin derived alcohols include hydrogenated rosin, available from Hercules under the tradename Abitol E, and chemical derivatives of rosin available from Arakawa Chemical under the tradename Pinecrystal.

Adhesives of the invention will typically comprise about 3% to about 20%, more preferably up to about 15%, of the rosin derived alcohol. The level will depend on the level of pressure sensitivity needed in the final adhesive and the amount and type of epoxidized block copolymer used. The alcohol acts as a chain transfer agent during cationic polymerization of the epoxy groups. Diols can act as crosslinkers whereas mono-ols will act to reduce the crosslink density and improve the adhesion of the crosslinked polymer through pendant rosin substituents. Diols used in excess (over the amount of epoxy) can also improve tack and reduce overall crosslink density. Mono-ols are most preferred. It has been discovered that use of a rosin alcohol produces a cured adhesive with more extensibility as measured by free swell in cyclohexane, which dissolves the saturated polymer and everything else that is not crosslinked. Peel and tack are also improved.

The adhesive compositions of this invention also may include an aliphatic or cycloaliphatic hydrocarbon resin with or without aromatic modification (preferably without), such as those derived from terpene monomers or from petroleum-derived monomers, as tackifier. Preferred are hydrogenated petroleum-derived hydrocarbon resins. Non-limiting examples include aliphatic olefin derived resins such as those available from Goodyear under the Wingtack® tradename and the Escorez® 1300 series from ExxonMobil. A common $C_5$ tackifying resin in this class is a diene-olefin copolymer of piperylene and 2-methyl-2-butene having a softening point of about 95° C. This resin is available commercially under the tradename Wingtack 95 and is prepared by the cationic polymerization of a mixture containing approximately 60% piperylene, 10% isoprene, 5% cyclo-pentadiene, 15% 2-methyl-2-butene and about 10% dimer, as taught in U.S. Pat. No. 3,577,398. The resins normally have ring and ball softening points as determined by ASTM method E28 between about 20° C. and 150° C. Also useful are C5/C9 aromatic/aliphatic olefin-derived resins available from ExxonMobil in the Escorez 2000 series. Hydrogenated hydrocarbon resins are especially useful when the long term resistance to oxidation and ultraviolet light exposure is required. These hydrogenated resins include such resins as the Escorez 5000 series of hydrogenated cycloaliphatic resins from ExxonMobil, hydrogenated $C_9$ and/or $C_5$ resins such as Arkon® P70, P90, P115, P125 supplied by Arakawa Chemical, hydrogenated aromatic hydrocarbon resins such as Regalrez® 1018, 1085 and the Regalite® R series of resins from Hercules Specialty Chemicals. Other useful resins include hydrogenated polyterpenes such as Clearon® P-105, P-115 and P-125 from the Yasuhara Yushi Kogyo Company of Japan. Preferred for use are hydrogenated, cyclic or $C_5$ resins, such as Escorez 5400 (ExxonMobil), a hydrogenated DCPD (dicylopentadiene) tackifier. Mixtures of two or more of the above-described resins may be preferred for some formulations.

Adhesives of the invention will typically contain from about 20% to about 70% of the hydrogenated resin, more preferably from about 30% to about 60%.

The adhesives of the invention may optionally contain a rosin and/or rosin ester. These tackifiers are added to improve the adhesion to various surfaces, especially polar surfaces such as glass, metal, or corona-treated plastics. Representative examples are natural and modified rosins including gum rosin, wood rosin, tall oil rosin, distilled rosin, hydrogenated rosin, dimerized rosin, and polymerized rosin; glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin.

The rosin and/or rosin ester will typically be used in amounts of up to about 25%. Rosin is preferred over rosin ester for maximum adhesion to polar substrates.

The adhesives of the invention may also comprise up to about 30% by weight of an oil diluent. Suitable oils include olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. Suitable oligomers include polypropylenes, polybutenes, hydrogenated polyisoprene, hydrogenated polybutadiene, or the like having average molecular weights between about 350 and about 10,000. Preferred are petroleum derived white oils such as Britol 35T, a paraffinic white oil and KAYDOL OIL a napthenic white oil, both of which are available from Witco Corporation.

The cationic photoinitiators are typically employed in concentrations ranging from about 0.01% by weight to about 10% by weight, preferably in amounts ranging from about 0.05% by weight to about 1% by weight, more preferably from about 0.1% by weight to about 0.5% by weight. Combinations of two or more photoinitiators may also be used.

Photosensitizers may be added to extend the spectral response to higher wavelengths. For example phenothiazine, perylene, and anthracene are effective sensitizers for both sulfonium and iodonium salts.

Combinations of photoinitiators may be used to achieve the best possible cure of adhesive compositions. Photoinitiators are preferably used in the least amount necessary to get initiation of cure at the line speed of the process. Cationic cure is inhibited by basic species such as amines or even water, and these must therefore be avoided or adequate photoinitiator added to overcome them.

Antioxidants are typically added to the commercially available compounds in order to protect the ingredients against degradation during preparation and use of the adhesive compositions. Combinations of antioxidants are often more effective due to the different mechanisms of degradation to which various polymers are subject. Certain hindered phenols, organo-metallic compounds, aromatic amines, aromatic phosphites, and sulphur compounds are useful for this purpose. Examples of effective types of these materials include phenolic antioxidants, thio compounds, and tris-(nonylated phenyl)phosphites. Again, care should be taken to minimize the use of basic antioxidants.

Examples of commercially available antioxidants include IRGANOX 1010 (pentaetythrityl-tetrakis[3-(3,5-di-tert-butyl-4-hydroxyphenyl)propionate); IONOL (2,6-di-tertiary-butyl-4-methyl phenol); IONOX 330 (3,4,6-tris(3,5-di-tertiary-butyl-p-hydroxybenzyl)-1,3,5-trimethylbenzene-); and POLYGARD HR (tris-(2,4-di-tertiary-butyl-phenyl)phosphite). The antioxidant chosen must not interfere with the radiation cure of the final composition. Irganox 1010 has been found to be suitable in combination with the photoinitiator UVI 6974.

To ensure long-term thermal stability, in general from about 0.1% to about 3% by weight of one or more antioxidants is included in the adhesive compositions, preferably from about 0.4% by weight to about 1.5% by weight.

Additional materials may be added optionally to the adhesive composition at up to about 15% by weight, preferably from about 5% by weight to about 10% by weight, dependent on the intended end-use of the adhesive. Such additional materials include, without limitation, unsaturated block copolymers of monovinyl aromatic hydrocarbons and conjugated dienes such as polystyrene-polybutadiene-polystyrene, polystyrene-polyisoprene-polystyrene, poly(alphamethyl-styrene)-polybutadiene-poly(alpha-methyl-styrene), poly(alpha-methyl-styrene)-polyisoprene-poly(alpha-methyl-styrene). Other polymers that can be added to modify adhesive properties include hydrogenated radial polyisoprene (for example Kraton G1750 sold by Kraton Polymers). Polyisobutylene, butyl rubber, polyisoprene, polybutadiene, and ethylene propylene random copolymers, and styrene butadiene random copolymers.

In addition to the above-described additional materials, the various compositions of the present invention may include other additives known to those skilled in the art. These additives may include, but are not limited to, pigments, fillers, waxes, fluorescent additives, flow and leveling additives, wetting agents, surfactants, antifoaming agents, rheology modifiers, and stabilizers. Preferred additives are those which do not have appreciable absorption in the wavelengths of interest and are not basic.

Examples of waxes include petroleum-derived such as paraffin wax, or synthetic waxes such as those produced by Fischer-Tropsch chemistry. Naturally derived waxes including non-reactive waxes and reactive waxes such as castor wax (which can react through its hydroxyl groups during cure).

Examples of pigments and filler materials include, but are not limited to, titanium dioxide, hydrophobic amorphous fumed silica, amorphous precipitated silica, carbon black, and polymer powders. Examples of flow and leveling additives, wetting agents, and antifoaming agents include silicones, hydrocarbons, fluorine-containing compounds, and non-silicone polymers and copolymers such as copolyacrylates.

Other materials which may be added optionally to the adhesive composition include endblock resins which are substantially aromatic. Examples of such endblock resins can be prepared from any substantially aromatic monomers having a polymerizable unsaturated group. Typical examples of such aromatic monomers include the styrenic monomers, styrene, alpha-methyl styrene, vinyl toluene, methoxy styrene, tertiary butyl styrene, chloro styrene, etc., indene monomers including indene, and methyl indene. The aromatic endblock resin is preferably present in amounts of 5 to 20 weight percent. Preferred is HERCOLITE 240 or KRISTALEX 5140, both of which are alpha methyl styrene resins available from Hercules, Inc.

One embodiment of the invention is directed to an adhesive comprising an epoxidized block copolymer, a saturated block copolymer, and a photoinitiator. The adhesives of the invention may optionally further comprise a hydrocarbon resin, a rosin derived alcohol, a rosin, rosin ester and/or an oil.

Another embodiment of the invention is directed to an adhesive comprising an epoxidized block copolymer, a rosin derived alcohol, and a photoinitiator. The adhesives of the invention may optionally further comprise a hydrocarbon resin, a saturated block copolymer, a rosin, rosin ester and/or an oil.

In a preferred embodiment of the present invention the adhesive composition comprises from about 15% to about 35% by weight of at least one epoxidized block copolymer, from about 5% to about 15% by weight of at least one saturated block copolymer, from about 30% to about 60% by weight of at least one hydrocarbon resin, from about 3 to about 15% of a rosin derived mono-ol, from about 0.02 to about 2.0% of a cationic photoinitiator, from about 0 to about 25% of a rosin and/or rosin ester, from about 0 to about 30% of a mineral oil, and from about 0 to about 2% of an antioxidant.

The adhesive compositions of the invention are prepared by conventional methods. As an example, the epoxidized block copolymer and saturated block copolymer or tackifying resin and other desired components may be blended at an elevated temperature, (e.g., temperature of about 300° F.) using an extruder, a Z-blade mixer or other conventional mixing device.

The adhesives of the present invention may be used to bond one substrate to a second substrate. Substrates include but are not limited to plastic, glass or plastic-coated glass, wood, metal, etc. The adhesive may be applied by a variety of methods including coating or spraying in an amount sufficient to cause the substrates to be bonded together to adhere. The adhesive coated substrate may be irradiated before or after bonding. Since cure begins immediately upon irradiation, but may not be completed for several days, there is time immediately after irradiation, but before gelation for bonding to take place. Ideally, the bond is made before irradiation for optimum wet out and adhesion.

The pressure sensitive adhesives of the invention may advantageously be used in the manufacture of adhesive articles including, but not limited to, industrial tapes and transfer films. Single and double face tapes, as well as supported and unsupported free films are encompassed by the invention. In one embodiment, the adhesive article comprises an adhesive coated on at least one major surface of a backing having a first and second major surface. Useful backing substrates include, but are not limited to foam, metal, paper, fabric, and various polymers such as polypropylene, polyamide, polyester, polyethylene terephthalate, and mixtures thereof. The adhesive may be present on one or both surfaces of the backing. When the adhesive is coated on both surfaces of the backing, they can be the same or different.

The following examples are provided for illustrative purposes only.

EXAMPLE 1

1-Chloro-4-hydroxythioxanthone was prepared as described in U.S. Pat. No. 5,414,092 (1995).

2,2'-Dithiobisbenzoic acid (15.3 g, 0.05 mol) was stirred in concentrated sulfuric acid (150 mL) at 10–20° C. and 4-chlorophenol (38.5 g, 0.3 mol) was added over 2 h. After stirring for an additional 1 h, the reaction was raised to 70–80° C. and stirred for 2 h. The mixture was cooled to room temperature and poured into ice water (500 mL). An orange solid was formed, filtered off, washed well with cold water and dried overnight under vacuum to give 1-chloro-4-hydroxythioxanthone (18.3 g, 70%) with mp 260–265° C. The identity of this compound was shown by $^1$H NMR to have the following structure:

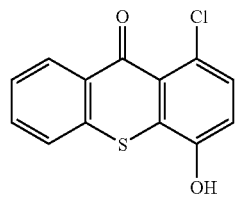

EXAMPLE 2

1,2-Dichloro-4-hydroxythioxanthone was prepared by a method similar to that described in Example 1. This compound was obtained with a 95% yield. The identity of this compound was shown by ¹H NMR to have the following structure:

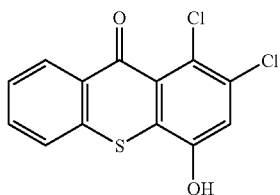

EXAMPLE 3

1-Chloro-4-hydroxy-2-methylthioxanthone was prepared by a method similar to that described in Example 1. This compound was obtained with a 76% yield. The identity of this compound was shown by ¹H NMR to have the following structure:

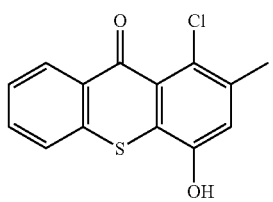

EXAMPLE 4

1-Chloro-4-hydroxy-3-methylthioxanthone was prepared by a method similar to that described in Example 1. This compound was obtained with a 89% yield. The identity of this compound was shown by ¹H NMR to have the following structure:

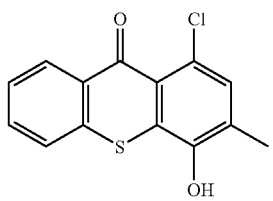

EXAMPLE 5

1-Chloro-4-dodecyloxythioxanthone was prepared as follows. A solution of 1-chloro-4-hydroxythioxanthone (14.0 g, 0.05 mol), K$_2$CO$_3$ (8.09, 0.06 mol) in acetone (250 mL) was stirred and refluxed for 10 min. Bromododecane (20.0 g, 0.08 mol) was added and the resulting mixture was stirred for 24 h under reflux. The reaction was then cooled to room temperature and quenched with water (500 mL). The obtained solid was filtered, washed with water, purified by recrystalized from isopropanol to give the 1-chloro-4-dodecyloxythioxanthone (14.3 g, 62%) with mp 79–80° C. The identity of this compound was shown by ¹H NMR to have the following structure:

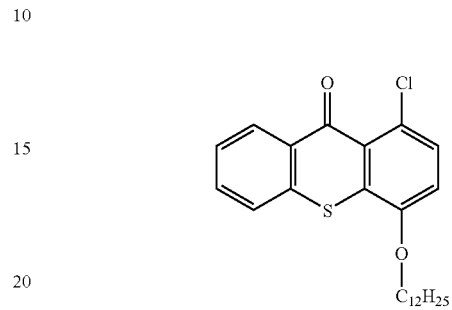

EXAMPLE 6

1,2-Dichloro-4-dodecyloxythioxanthone was prepared by a method similar to that described in Example 5. 1,2-Dichloro-4-dodecyloxythioxanthone was obtained with a 46% yield and mp 70–72° C. The identity of this compound was shown by ¹H NMR to have the following structure:

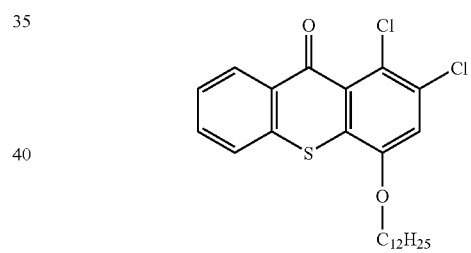

EXAMPLE 7

1-Chloro-4-dodecyloxy-2-methylthioxanthone was prepared by a method similar to that described in Example 5. 1-Chloro-4-dodecyloxy-2-methylthioxanthone was obtained with a 65% yield and mp 63–64° C. The identity of this compound was shown by ¹H NMR to have the following structure:

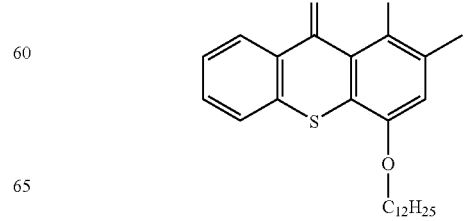

EXAMPLE 8

1-Chloro-4-dodecyloxy-3-methylthioxanthone was prepared by a method similar to that described in Example 5. 1-Chloro-4-dodecyloxy-3-methylthioxanthone was obtained with a 65% yield and mp 63–65° C. The identity of this compound was shown by $^1$H NMR to have the following structure:

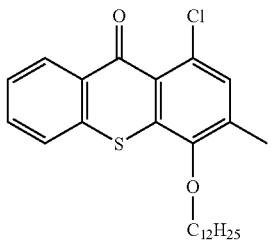

EXAMPLE 9

A sulfonium salt containing 1-chloro-4-dodecyloxythioxanthone from Example 5 was prepared as follows. A solution of 1-chloro-4-dodecyloxythioxanthone (4.0 g, 9.3 mmol), diphenylsulfoxide (1.9 g, 9.3 mmol) in dichloromethane (50 mL) and acetic anhydride (30 mL) was stirred at 0–10° C. Concentrated sulfuric acid (98%, 4.0 g, 40 mmol) was added slowly. The reaction was then warmed to room temperature and stirred for 48 h. Water (30 mL) and NaSbF$_6$ (2.5 g, 9.7 mmol) were then added and the mixture was stirred at room temperature for an additional 12 h. The mixture was washed with water and the organic layer was dried with MgSO$_4$. After removal of the solvent, the obtained solid was recrystalized from MeOH at room temperature to give the sulfonium salt as a yellow solid (1.8 g, 23–50%). The identity of this compound was shown by $^1$H NMR to have the following structure:

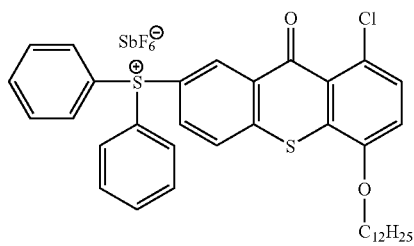

EXAMPLE 10

A sulfonium salt containing 1,2-dichloro-4-dodecyloxythioxanthone from Example 6 was prepared by a method similar to that described in Example 9. After removal of the solvent, the obtained solid was recrystalized from MeOH to give the title sulfonium salt as an orange solid. The identity of this compound was shown by $^1$H NMR to have the following structure:

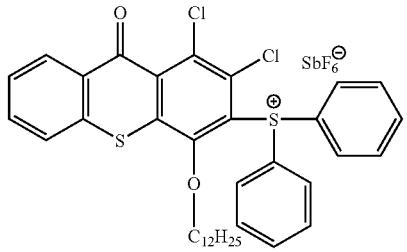

EXAMPLE 11

A sulfonium salt containing 1-chloro-4-dodecyloxy-2-methylthioxanthone from Example 7 was prepared by a method similar to that described in Example 9. After removal of the solvent, the obtained solid was recrystalized from MeOH to give the title sulfonium salt as an orange solid. The identity of this compound was shown by $^1$H NMR to have the following structure:

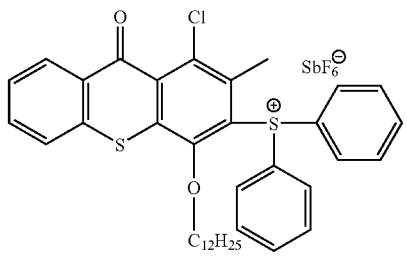

EXAMPLE 12

A sulfonium salt containing 1-chloro-4-dodecyloxy-3-methylthioxanthone from Example 8 was prepared by a method similar to that described in Example 9. After removal of the solvent, the obtained solid was recrystalized from MeOH to give the title sulfonium salt as an orange solid. The identity of this compound was shown by $^1$H NMR to have the following structure:

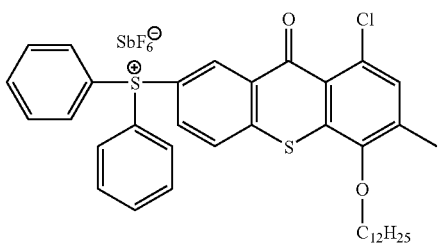

EXAMPLE 13

A sulfonium salt containing 1-chloro-4-propoxythioxanthone from Aldrich was prepared by a method similar to that described in Example 9. After removal of the solvent, the obtained solid was recrystalized from MeOH to give the title sulfonium salt as an orange solid. The identity of this compound was shown by $^1$H NMR to have the following structure:

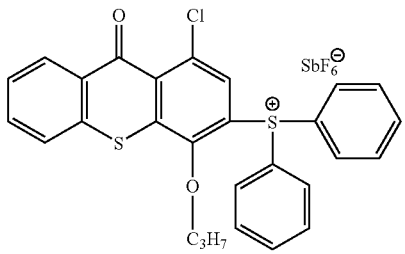

EXAMPLE 14

1-Bromo-2-decyl-1-tetradecane was prepared by the bromonation of 2-decyl-1-tetradecanol according to a method described in the *Journal of Organic Chemistry*, 42, 353, 1997.

A solution of 2-decyl-1-tetradecanol (50.0 g, 0.14 mol) and CBr$_4$ (58.0 g, 0.17 mol) in dichloromethane (150 mL) was stirred at 0° C. and PPh$_3$ (55.0 g, 0.21 mol) was added portionwise. After the addition of PPh$_3$, the reaction mixture was stirred for additional 2 h at 0° C. Reaction solvent was then removed and the mixture was washed with methanol to remove the by-product phosphine oxide. The resulting viscous liquid was further purified by extracting with hexane to give 1-bromo-2-decyl-1-tetradecane (53.6 g, 91%). This compound was shown by $^1$H NMR and GC-MS to have the following structural formula:

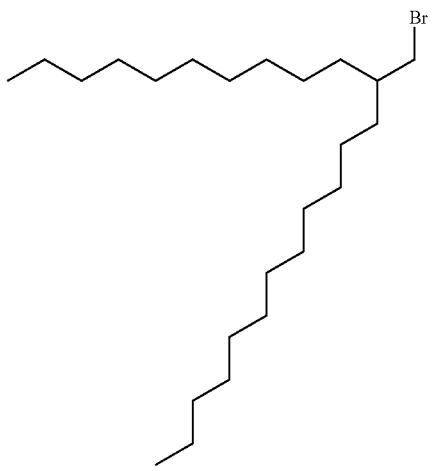

EXAMPLE 15

1-Chloro-4-(2-decyltetradecyl-1-oxy)thioxanthone was prepared by a method similar to that described in Example 5. 1-Chloro-4-(2-decyltetradecyl-1-oxy)thioxanthone was obtained with a 42% yield and mp 50–51° C. The identity of this compound was shown by $^1$H NMR to have the following structure:

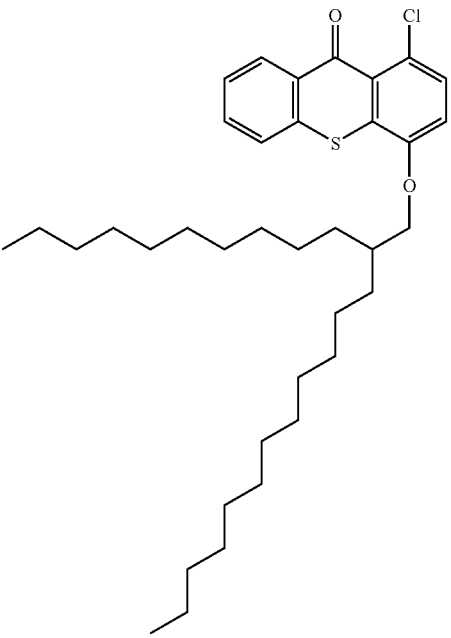

EXAMPLE 16

A sulfonium salt containing 1-chloro-4-(2-decyltetradecyl-1-oxy)thioxanthone from Example 15 was prepared as follows. A solution of 1-chloro-4-(2-decyltetradecyl-1-oxy)thioxanthone (1.68 g, 2.8 mmol), diphenylsulfoxide (0.57 g, 2.8 mmol) in dichloromethane (50 mL) was stirred at 10–20° C. Eaton's reagent (P$_2$O$_5$/MSA 1:10) (20 mL) was added slowly. The reaction was then warmed to room temperature and stirred for 48 h. Water (30 mL) and NaSbF$_6$ (0.8 g, 2.9 mmol) were then added and the mixture was stirred at room temperature for additional 12 h. The mixture was washed with water and the organic layer was dried with MgSO$_4$. After removal of the solvent, the obtained solid was recrystalized from MeOH to give the title sulfonium salt as a yellow solid (1.9 g, 66%). The identity of this compound was shown by $^1$H NMR to have the following structure:

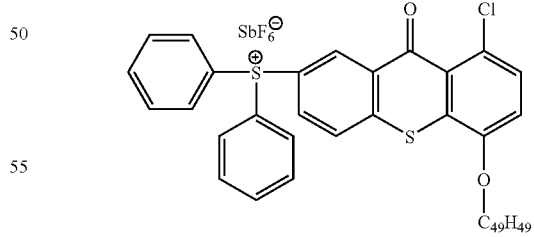

EXAMPLE 17

2',5-dichloro-2-dodecyloxybenzophenone was prepared by a method similar to that described in Example 5. 2',5-Dichloro-2-dodecyloxybenzophenone was obtained with a 37% yield and mp 30–32° C. The identity of this compound was shown by $^1$H NMR to have the following structure:

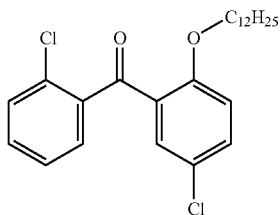

EXAMPLE 18

A sulfonium salt containing 2',5-dichloro-2-dodecyloxy-benzophenone was prepared by a method similar to that described in Example 9. After removal of the solvent, the obtained solid was recrystalized from MeOH to give the title sulfonium salt as a light yellow solid. The identity of this compound was shown by $^1$H NMR to have the following structure:

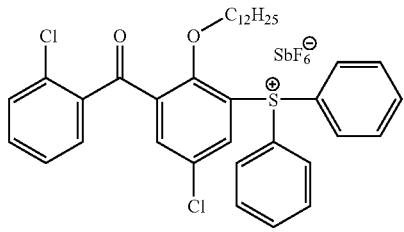

EXAMPLE 19

4,4'-Didodecyloxyphenyl sulfide and 4,4'-didodecyloxy-1phenyl sulfoxide were prepared using a method described in U.S. Pat. No. 5,010,118. 4,4'-didodecyloxyphenyl sulfide and 4,4'-didodecyloxylphenyl sulfoxide. The structures of 4,4'-didodecyloxyphenyl sulfide and 4,4'-didodecyloxylphenyl sulfoxide are as follows:

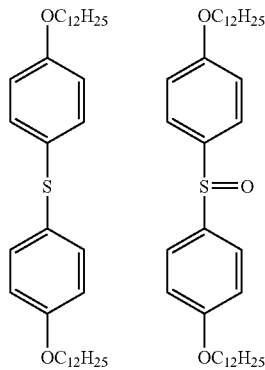

EXAMPLE 20

A sulfonium salt containing 1-chloro-4-propoxythioxan-thone and bis(dodecyloxy) substituted phenyl groups was prepared as follows. A solution of 1-chloro-4-dodecyoxythioxanthone (2.1 g, 6.9 mmol), 4,4'-didodecylphenylsulfoxide (4.0 g, 7.0 mmol) in chloroform (100 mL) and acetic anhydride (25 mL) was stirred at 10–20° C. Concentrated sulfuric acid (98%, 4.0 g, 40 mmol) was added slowly. The reaction was then warmed to room temperature and stirred for 48 h. Water (30 mL) and NaSbF$_6$ (2.0 g, 7.7 mmol) were then added and the mixture was stirred at room temperature for additional 12 h. The mixture was washed with water and the organic layer was dried with MgSO$_4$. After removal of the solvent, the obtained solid was recrystalized from MeOH to give a sulfonium salt as an orange solid. The identity of this compound was shown by $^1$H NMR to have the following structure:

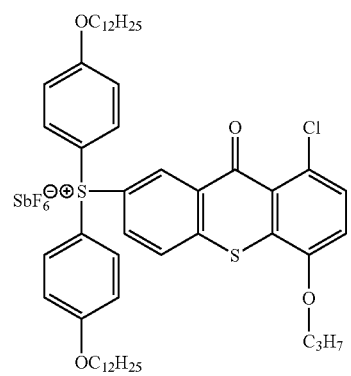

EXAMPLE 21

A sulfonium salt containing 1-chloro-4-dodecyloxy-thioxanthone was prepared by a method similar to that described in Example 9. After removal of the solvent, the obtained solid was recrystalized from MeOH at −20° C. to give the sulfonium salt as light orange crystals in 20–45% yield with a mp of 99–105° C. The identity of this compound was shown by $^1$H and other NMR spectroscopy to have the following structure:

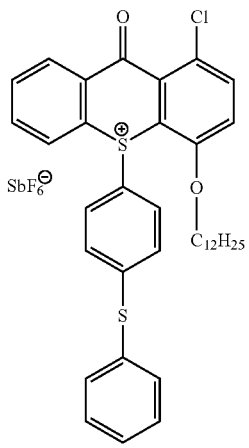

EXAMPLE 22

1-chloro-4-propyloxy-10-oxythioxanthone was prepared as follows. A solution of 1-chloro-4-propyloxy-thioxanthone (5.0 g, 0.016 mol) in acetonitrile (400 mL) and water (80 mL) was stirred at room temperature. Ammonium cerium (IV) nitrate (44 g, 0.080 mol) was added and the resulting mixture was stirred for 2 h at room temperature. The reaction was followed by GC-MS. The reaction mixture was then quenched with water (500 mL) and was extracted with chloroform. After removal of the solvent, the obtained solid was recrystalized from benzene to give the title product as yellow crystals with mp 155–157° C. The identity of this compound was shown by ¹H NMR and GC-MS to have the following structure:

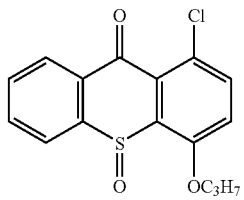

EXAMPLE 23

1-chloro-4-dodecyloxy-10-oxythioxanthone was prepared by a method similar to that described in Example 22. The identity of this compound was shown by ¹H NMR to have the following structure:

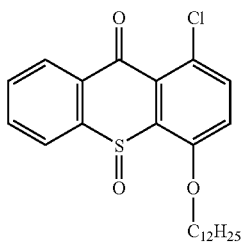

EXAMPLE 24

1-chloro-4-propyloxy-10-oxythioxanthone was prepared by a method similar to that described in Example 22. The identity of this compound was confirmed by ¹H NMR and GC-MS to have the following structure:

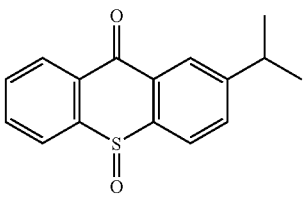

EXAMPLE 25

1-chloro-4-dodecyloxy-10-oxythioxanthone was prepared by a method similar to that described in Example 9. The identity of this compound was confirmed by ¹H NMR to have the following structure:

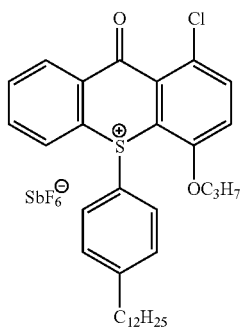

EXAMPLE 26

Another approach to synthesize the same sulfonium salt as shown in Example 21 is to react 1-chloro-4-dodecyloxy-10-oxythioxanthone from Example 23 with diphenyl sulfide, using the similar reaction condition described in Example 9. After removal of the solvent, the obtained solid was recrystalized from MeOH at −20° C. to give the sulfonium salt in <50% yield. The identity of this compound was confirmed by ¹H NMR to have the following structure:

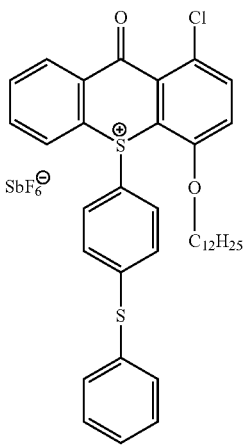

EXAMPLE 27

1-chloro-4-dodecyloxy-sulfoxyxanthone was prepared was prepared by a method similar to that described in Example 9. The identity of this compound was confirmed by ¹H NMR to have the following structure:

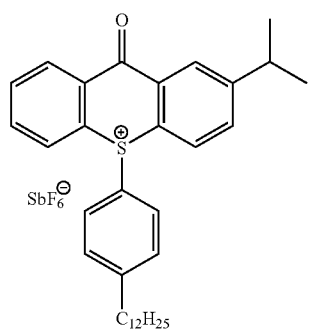

EXAMPLE 28

A sulfonium salt containing 1-chloro-thioxanthone and bis(dodecyloxy) substituted phenyl groups was prepared by a method similar to that described in Example 9. After removal of the solvent, the obtained solid was recrystalized from MeOH to give the title sulfonium salt as a light orange solid. The identity of this compound was confirmed by ¹H NMR to have the following structure:

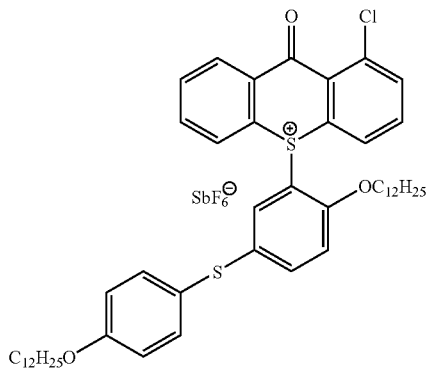

EXAMPLE 29

EKP 207 epoxy polymer (20 g) was mixed with 0.1 g of the sulfonium salt of Example 21. The appearance of the obtained formulation was clear even after being heated for 2 h at 100° C., and the UV cure rate did not change relative to an unheated sample. A similar sample prepared with the commercially available sulfonium salt Cyracure UVI-6974 (Union Carbide) was hazy, especially after being heated at 100° C. for 2 h. The UV cure rate of the heated sample containing UVI-6974 decreased dramatically in comparison with that of unheated one. The formulations were irradiated by using either H or D bulbs medium pressure mercury lamps (Fusion UV Systems).

EXAMPLE 30

Three formulated samples were prepared with EKP 207 epoxy polymer (20 g) and, as photoinitiator (0.1 g, 0.5% wt), the sulfonium salt from Example 21, UVI-6974 or UV9380C (a commercially available iodonium salt available from GE Silicones. As can be seen in FIG. 1, based on photoDSC analysis, the UV cure rate of the sample containing the sulfonium salt from Example 21 is faster than the formulations containing UVI-6974 or UV9380C as the photoinitiators. A medium pressure mercury arc lamp at room temperature was used for photoDSC analyses.

EXAMPLE 31

A photoreactive hot-melt pressure sensitive adhesive composition was prepared by mixing the following components in a hot melt mixer: 32% (by weight) of EKP 207, 15 parts of Kraton GPR 6919 (Kraton Polymers), 52 parts of Escorez 5400 (ExxonMobil), 0.5% of Irgnox1010 (Ciba-Geigy), and 0.2% of the photoinitiator of Example 21. The formulation was coated on a PET film (3 mil film thickness) and the film was irradiated for 5 seconds under a Hg lamp with peak power and dosage of UV V 373 mW/cm$^2$, 323 mJ/cm$^2$; UV A 635 mW/cm$^2$, 549 mJ/cm$^2$; UV B 620 mW/cm$^2$, 544 mJ/cm$^2$. The adhesive film was fully cured based on RDA analysis.

EXAMPLE 32

A varnish formulation was prepared by mixing the following components: 95.9% (by weight) of UVR 6110 (UCB Chemicals, a cycloaliphatic epoxide), 0.1% Tegorad (TeGo, wetting aid), and 4% of a photoinitiator from Example 21 or UVI-6974. The UV cure rate of the varnish sample containing the sulfonium salt from Example 21 was much faster relative to the sample containing UVI-6974, based on photoDSC analysis.

EXAMPLE 33

Two coating/sealant compositions were formulated as follows:

Formula 1: Epon 862 (Resolution Chemical): 8.00 g
  proprietary UV cure diluent/accelerator package: 2.00 g
  photoinitiator from Example 21:0.08 g
  talc (Luzenac Americas): 6.7 g Formula 2: Epon 862:8.00 g
  proprietary UV cure diluent/accelerator package: 2.00 g
  Rhodorsil 2074 iodonium salt (Rhodia): 0.08 g
  talc 6.7 g.

Films of both formulations were formed using a 4 mil drawdown bar onto PTFE-coated aluminum plates. Films were cured without any filter, and also with a 7 mm thick ITO-coated sodalime glass filter between the lamp and the sample. This filter essentially absorbs all light of wavelengths less than ~320 nm, and passes 100% intensity above ~330 nm. The films were cured using a Dymax stationary curing unit, which provided intensities of 45 mW/cm$^2$ UVA & 32.5 mW/cm$^2$ UVB without the filter and 35 mW/cm$^2$ UVA & 0 mW/cm$^2$ UVB with the filter in place. The results at various cure times are provided in Table 1.

TABLE 1

| Formula & Cure time | No filter | with ITO-glass filter |
| --- | --- | --- |
| Formula 1, 20 s | fully cured | fully cured |
| Formula 1, 40 s | fully cured | fully cured |
| Formula 1, 60 s | fully cured | fully cured |
| Formula 2, 20 s | fully cured | very little cure |
| Formula 2, 40 s | fully cured | partially cured, very sticky surface |
| Formula 2, 60 s | fully cured | partially cured, tacky surface |

As can be seen from the data, both formulations cured well without the glass filter. Conversely, only the red-shifted inventive photoinitiator of Example 21 efficiently cured the formulation when the glass filter was in place. The Rhodorsil 2074 photoinitiator does not absorb sufficient light at wavelengths above the cutoff wavelength of the filter, whereas the inventive sulfonium salt of Example 21 has strong absorbance bands above 330 nm, and is thus essentially unaffected by the glass filter.

EXAMPLE 34

Formulation 1 detailed in Example 32 was used as an adhesive composition to bond quartz glass die to sodalime glass substrates as follows. Films were made of the formulation using a 4 mil drawdown bar, and quartz die (4 mm×4 mm, cleaned by soaking in isopropyl alcohol followed by air drying) were placed on the uncured adhesive film. The die were then removed and placed on sodalime glass substrates (cleaned by wiping with an acetone-soaked lint-free cloth followed by air drying). Light pressure was applied to facilitate wet-out of the sodalime glass substrate by the adhesive on the quartz die. An ITO-coated glass filter (described in Example 32) was placed over the samples, and the samples were cured in a Dymax stationary curing unit (described in Example 32) for 40 seconds.

The samples were then evaluated for shear strength using a Royce die shear tester. The average die shear strength was found to be ca. 10 kgf, which is a value typical of cured epoxy adhesives within this testing geometry and protocol. As noted in Example 32, it is clear that the long wavelength absorbance properties of the inventive sulfonium salts allows them to cure efficiently even with common glass filters in place. This differentiates them from most unsensitized onium salt photoinitiators of the prior art.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A sulfonium salt photoinitiator having the structural formula:

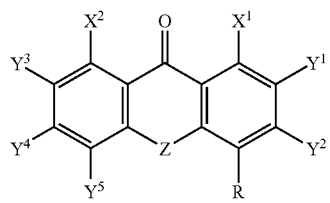

where
$X^1$ is Cl, Br, I, or F,
$X^2$ is Cl, I, F, H, alkyl or alkoxy,
$Y^1$, $Y^2$, $Y^3$, $Y^4$ and $Y^5$ are independently H, R, or $X^{1\ or\ 2}$,
Z is $SAr^+ \cdot M^-$, wherein Ar is phenyl, $C_{1-24}$ alkyl phenyl, $C_{1-24}$ alkoxyphenyl, acyl, thiophenyl, phenylthiophenyl, phenylsulfoxyphenyl, phenylsulfonylphenyl, $C_{1-24}$ alkylthiophenyl, $C_{1-24}$ dialkyl substituted phenylthiophenyl, or $C_{1-24}$ dialkoxy substituted phenylthiophenyl, and $M^-$ is $SbF_6^-$, $PF_6^-$, $AsF_6^-$, $BF_4^-$, $B(C_6F_5)_4^-$ or $Ga(C_6F_5)_4^-$, and
R is $C_{1-24}$ alkoxy, $C_{1-24}$ alkyl, aryl, Cl, Br, I, or F.

2. The photoinitiator of claim 1 having the structural formula:

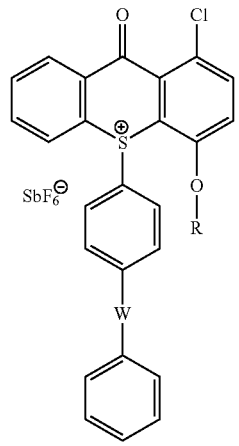

where R is $C_3H_7$, $C_{12}H_{25}$ or $C_{24}H_{49}$, W is S, SO, $SO_2$ or CO.

3. The photoinitiator of claim 2 where W is S and R is $C_3H_7$ or $C_{12}H_{25}$.

4. The photoinitiator of claim 2 where W is SO and R is $C_3H_7$ or $C_{12}H_{25}$.

5. The photoinitiator of claim 1 having the structural formula:

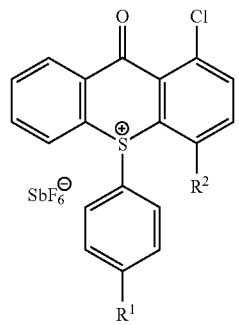

where $R^1$ and $R^2$ are independently $CH_3$, $C_2H_5$, $C_3H_7$, $C_{12}H_{25}$, $C_{24}H_{49}$, $OCH_3$, $OC_2H_5$, $OC_3H_7$, $OC_{12}H_{25}$ or $OC_{24}H_{49}$.

6. The photoinitiator of claim 5 where $R^1$ is $C_3H_7$ or $C_{12}H_{25}$ and $R^2$ is $OC_3H_7$ or $OC_{12}H_{25}$.

7. The photoinitiator of claim 6 where $R^1$ is $C_{12}H_{25}$ and $R^2$ is $OC_3H_7$.

8. A photocurable composition comprising the photoinitiator of any of claims 1, 2, 5 or 6.

9. The composition of claim 8 which is a photocurable adhesive, coating or sealant composition.

10. The composition of claim 9 which is a photocurable hot melt adhesive.

11. The compound 2-decyl-1-tetradecyl bromide.

* * * * *